United States Patent [19]

Puritch et al.

[11] Patent Number: 5,035,741

[45] Date of Patent: Jul. 30, 1991

[54] FATTY ACID BASED EMULSIFIABLE CONCENTRATE HAVING HERBICIDAL ACTIVITY

[75] Inventors: George S. Puritch, Saanichton; Roderick Bradbury, Sidney; Wenda Mason, Brentwood Bay, all of Canada

[73] Assignee: Safer, Inc., Newton, Mass.

[21] Appl. No.: 421,376

[22] Filed: Oct. 13, 1989

[51] Int. Cl.$^5$ .......................................... A01N 37/02
[52] U.S. Cl. .................................. 71/113; 71/DIG. 1
[58] Field of Search ........................... 71/DIG. 1, 113

[56] References Cited

U.S. PATENT DOCUMENTS

| | | | |
|---|---|---|---|
| 2,626,862 | 1/1953 | Zimmerman et al. | 71/113 |
| 3,645,716 | 2/1972 | Rutkowski | 71/113 |
| 3,932,405 | 1/1976 | Schonbeck et al. | 71/92 |
| 4,631,295 | 12/1986 | Engel et al. | 514/558 |

FOREIGN PATENT DOCUMENTS 49-25131  3/1974  Japan .

OTHER PUBLICATIONS

Puritch, "Pesticidal Soaps and Adjunants and How Do They Work", Proceedings of the 23rd Annual Lower Mainland, Horticultural Improvement Association Growers Short Course Feb. 11, 12, and 13, 1981, Abbotsford, B. C.

*Primary Examiner*—Glennon H. Hollrah
*Assistant Examiner*—Brian Bembenick
*Attorney, Agent, or Firm*—Lahive & Cockfield

[57] ABSTRACT

An environmentally compatible herbicidal composition comprises a fatty acid active ingredient, an oil component and an emulsifier component. The composition is a foliar applied herbicide which effectively controls a variety of unwanted weed and grass species.

The fatty acid component of the herbicidal composition comprises pelargonic acid which may be used alone or as the predomiannt component of a mixture of fatty acids including caprylic, pelargonic, capric, undecanoic, and lauric acids. The oil component comprises a triglyceride (e.g., various vegetable oils), a terpenoid-based oil or a paraffinic mineral oil. The emulsifier component comprises one or more anionic or nonionic emulsifiers.

12 Claims, No Drawings

FATTY ACID BASED EMULSIFIABLE CONCENTRATE HAVING HERBICIDAL ACTIVITY

BACKGROUND OF THE INVENTION

The present invention relates to pesticidal compositions having herbicidal activity. More particularly, the invention relates to environmentally compatible herbicides.

The term "pesticide" is used herein in a generic sense and includes insecticides, fungicides, herbicides and miticides. A variety of pesticides are well known and are widely used in agricultural, commercial and household applications. Although useful in controlling insect and mite populations as well as the growth of unwanted flora and fungi, many pesticides have been found to be harmful to the environment as well as to humans, other mammals, birds and fish.

Recently, salts of fatty acids, primarily sodium or potassium fatty acid salts, have been used commercially as pesticides. Compositions having excellent pesticidal properties which exploit these salts are available commercially from Safer, Inc., under the trademark SAFER INSECTICIDAL SOAP. A herbicidally active composition utilizing partially saponified fatty acids as the active ingredient is sold by Safer, Inc. under the trademark SHARPSHOOTER. These fatty acid salts are effective, naturally occurring pesticides which have no known long term environmental effects. Although such fatty acid salts are effective herbicides, it would be desirable to provide an alternative composition having an unsaponified active ingredient while maintaining the environmental compatibility of the pesticide and reducing the eye and skin irritancy of the product.

It is thus an object of this invention to provide an improved, environmentally compatible herbicidal composition. It is also an object to provide an effective herbicidally active composition with reduced eye and skin corrosivity. Another object is to provide an effective herbicidal composition which may be easily formulated in a storage-stable concentrated mixture and which may readily be formed into a usable emulsion by dilution with water. Other objects of the invention will be apparent from the description and claims which follow.

SUMMARY OF THE INVENTION

The present invention features an environmentally compatible herbicidal composition, comprising a fatty acid active ingredient, an oil component and an emulsifier component. This composition exhibits effective, broad-spectrum herbicidal activity. Moreover, the composition is a contact herbicide which has little or no residual soil activity as the composition is rapidly degraded and used as a nutrient source by soil microorganisms. The composition is also substantially non-toxic to humans and animals, and is not corrosive to the eyes and skin.

The composition typically is prepared in the form of a single phase, emulsifiable concentrate which includes active ingredient (i.e., fatty acid), the oil component and the emulsifier component. The emulsifier is present in order to facilitate the formation of an emulsion between the emulsifiable concentrate and an aqueous diluent, such as water, to yield a ready-to-use composition.

The fatty acid component of the herbicidal composition comprises one or a mixture of alpha monocarboxylic fatty acids having a hydrocarbon chain with between 8 and 12 carbon atoms. Pelargonic acid is the preferred fatty acid, and it may be used alone or in combination with other fatty acids.

The oil component of the herbicidal formulation comprises a mineral oil, a triglyceride or terpenoid-based oils. Preferred mineral oils include natural petroleum distillates comprising medium to long chain paraffinic hydrocarbons. Preferred triglycerides include cottonseed oil, soybean oil, sunflower oil, linseed oil, coconut oil, and other vegetable oils. Preferred terpenoid-based oils include pine oil, eucalyptus oil, cedar oil and the like.

Preferred emulsifiers include one or more anionic and/or nonionic emulsifiers of the type typically used in agricultural applications. The most preferred emulsifiers are those which are non-toxic and environmentally compatible.

The composition of the invention preferably is embodied as an emulsifiable concentrate, which is easily shipped and stored, and subsequently may be diluted with water before use. The emulsifiable concentrate has a relatively high concentration of active ingredient. This formulation approach facilitates the use of smaller containers of a concentrated formulation which subsequently may be diluted with water to yield a ready-to-use product. The emulsifiable concentrate may comprise from approximately 20% to 80% active ingredient. More preferably, the active ingredient present in the concentrate ranges between 30% and 60%. The concentration of oil component and emulsifier component in the concentrate ranges from about 15% to 75% and 2% to 10%, respectively. In a most preferred embodiment the concentrate comprises approximately 40% fatty acid, 55% oil component and 5% emulsifier component. To prepare a ready-to-use formulation, the concentrate is diluted with water so as to contain approximately 1% to 8% active ingredient and commensurately dilute concentrations of the oil and emulsifier components.

All percentages shown in this disclosure represent percent by weight, unless otherwise noted.

DETAILED DESCRIPTION OF THE INVENTION

The herbicidal composition of this invention comprises an aqueous emulsion having one or more fatty acids as the active ingredient, an oil component and one or more emulsifiers. Typically, the composition is prepared in the form of an emulsifiable concentrate which includes 20% to 80% fatty acid component, 15% to 75% oil component, and 2% to 10% emulsifier. In a preferred embodiment, the fatty acid component comprises about 40% of the composition, and the oil and emulsifier components respectively comprise approximately 55% and 5% of the composition. The emulsifiable concentrate is diluted with water before use to achieve a ready-to-use composition having the fatty acid component present in the range of approximately 1.0 to 8.0 weight percent, the oil component present in the range of about 1.3% to 11.0% and the emulsifier component present in the range of about 0.125% to 1.0%.

The fatty acid component of the herbicidal composition of this invention comprises one or a mixture of alpha monocarboxylic fatty acids having a hydrocarbon chain with between 8 and 12 carbon atoms. Preferably, the fatty acid is pelargonic acid, which may be used alone or as the major constituent (i.e., about 90%) of a mixture which includes other fatty acids. In one preferred embodiment the fatty acid component comprises a mixture of pelargonic acid, caprylic and capric acids wherein pelargonic acid accounts for most of the mixture and caprylic and capric acids are present in relatively small amounts. Such a mixture, having about 94% pelargonic acid, 4% caprylic acid and 2% capric acid, is commercially available under the trademark "EMERY 1202" from Emery Division, Quantum Chemical Corporation, Cincinnati, Ohio. In another embodiment, pelargonic acid may be combined with undecanoic acid and utilized as the active ingredient of the herbicidal composition.

The fatty acid components set forth above are examples of currently preferred fatty acids and fatty acid mixtures. It is expected that the ratios of the various constituents of these fatty acids and mixtures may be altered, or that other combinations of fatty acids having between 8 and 12 carbon atoms may be used to obtain the same or better results. Preferably, the active ingredient is an unsaponified single fatty acid or a mixture of unsaponified fatty acids.

The oil component of the present invention preferably is a terpenoid, a triglyceride, or a mineral oil. The terpenoid-based oils which may be used with this invention include pine oil, eucalyptus oil, orange oil, cedar oil and the like. Useful triglycerides include various vegetable oils such as cottonseed oil, linseed oil, coconut oil, various grades of soybean oil (e.g., crude soybean oil, degummed soybean oil, salad grade soybean oil), sunflower oil, olive oil, grape oil, rapeseed oil and mustard oil. Cottonseed oil is currently the most preferred triglyceride. The mineral oils which may be used with the herbicidal formulation of this invention are refined horticultural oils such as paraffinic, natural petroleum distillates. An example of a preferred mineral oil is commercially available under the trademarks "SUNSPRAY 6E", "SUNSPRAY 6N" and "SUNSPRAY 6E PLUS" from Sun Refining and Marketing Company of Philadelphia, Pa. Such a product contains about 99% refined petroleum distillates and about 1% emulsifier.

Cottonseed oil is the most preferred oil component for use with the present herbicidal formulation due to its low toxicity to humans and animals, its environmental compatibility and also because the phytotoxicity of the compositions which contain it. Pine, olive and sunflower oils each may be effectively used in herbicidal compositions to provide similar levels of phytotoxicity. However, factors such as high cost, strong odor, or both, render such oils less favorable than cottonseed oil. It is understood that other triglycerides or terpenoid-based oils may be effectively used in a herbicidal formulation falling within the scope of this invention. Moreover, mineral oils may be used in such a herbicidal formulation with equal or superior herbicidal characteristics to a formulation utilizing cottonseed oil.

The emulsifier component of the formulation comprises one or more anionic and/or nonionic emulsifiers. The most preferred emulsifiers are those which facilitate the formation of a suitable emulsion of the concentrate with an aqueous diluent. In addition, preferred emulsifiers are those which are non-toxic and environmentally compatible. Suitable emulsifiers used in formulating the herbicidal composition of this invention include alkyl aryl sulfonate-based emulsifiers and polyoxyethylene derivatives of fatty acid partial esters of sorbitol anhydrides. Preferred, commercially available emulsifiers include those sold under the trademark "Atlox" (e.g., Atlox 3404F and Atlox 3409F) by Atkemix Inc. of, as well as those also sold by Atkemix, Inc. under the trademark "Tween" (e.g., Tween 80). "Emsorb 6900" sold by Quantum Chemicals of Cincinnati, Ohio is another used commercially available emulsifier which may be useful interchangeably with "Tween 80". The specific emulsifiers identified above are provided only as examples of those which are currently preferred. One skilled in the art will readily be able to choose other emulsifiers which perform as well as, or perhaps better than, the emulsifier compounds identified above.

Many combinations of fatty acid component, oil component and emulsifier component may be used to obtain a herbicidal composition having effective phytotoxicity. A concentrated herbicidal composition according to this invention may include about 20–80% fatty acid, 15–75% oil component and 2–10% emulsifier component. Most preferably the herbicidal concentrate comprises 40% fatty acid, 55% oil component and 5% emulsifier component. The concentrated formulation may be sold commercially and subsequently diluted with water by an end user, or it may be sold in a pre-diluted, ready-to-use state. In any event, a ready-to-use formulation of this herbicide preferably contains about 1–8% fatty acid active ingredient 1.3–11.0% oil component and 0.125–1.0% emulsifier component.

Examples of various preferred herbicidal formulations are shown below in Table I. This table identifies an emulsifiable concentrate of the invention which may be diluted with water to obain a ready-to-use herbicide having fatty acid concentrations ranging from 1.0–8.0%, and commensurate dilutions of the oils and emulsifier components. In view of this disclosure one having ordinary skill in the art may prepare additional or alternative herbicidal formulations with equal or better efficacy simply by substituting other known emulsifiers or changing the concentrations of emulsifiers. Alternative formulations may also be prepared by making slight modifications in the amount of fatty acid and oil used.

TABLE I

| Preferred Herbicidal Emulsifiable Concentrate | |
|---|---|
| Formulation | Components (percent by weight) |
| A | 40% Fatty Acid* |
|   | 55% Cottonseed Oil |
|   | 1% Atlox 3409F |
|   | 2% Atlox 3404F |
|   | 2% Emsorb 6900** |
| B | 40% Fatty Acid* |
|   | 55% Pine Oil |
|   | 2.5% Tween 80 |
|   | 2.5% Atlox 3409F |
| C | 40% Fatty Acid* |
|   | 55% Sunspray 6E Plus Mineral Oil |
|   | 1% Atlox 3409F |
|   | 2% Atlox 3404F |
|   | 2% Emsorb 6900 |
| D | 80% Fatty Acid* |
|   | 15% Cottonseed Oil |
|   | 1% Atlox 3409F |
|   | 2% Atlox 3404F |
|   | 2% Emsorb 6900 |
| E | 20% Fatty Acid* |
|   | 75% Cottonseed Oil |
|   | 1% Atlox 3409F |
|   | 2% Atlox 3404F |
|   | 2% Emsorb 6900** |
| F | 20% Fatty Acid* |
|   | 75% Sunoil 6E Plus Mineral Oil |

TABLE I-continued

| Preferred Herbicidal Emulsifiable Concentrate | |
|---|---|
| Formulation | Components (percent by weight) |
| | 1% Atlox 3409F |
| | 2% Atlox 3404F |
| | 2% Emsorb 6900** |
| G | 60% Fatty Acid* |
| | 35% Cottonseed Oil |
| | 1% Atlox 3409F |
| | 2% Atlox 3404F |
| | 2% Emsorb 6900** |

*The fatty acid component of Table I comprises a mixture containing about 94% pelargonic acid, 2% capric acid and about 4% caprylic acid.
**Tween 80 may be substituted for this emulsifier.

The present herbicidal composition may be prepared through a variety of known formulation and mixing techniques well known to the art. One preferred formulation technique involves charging a stainless steel or high density polyethylene tank, equipped with a paddle stirrer, with the desired amount of the oil component and to commence high speed paddle stirring at approximately 150 rpm. The fatty acid component is then added while stirring is continued for about 15 minutes. Next, the emulsifier component is added and the mixture is stirred for an additional 30 minutes. This process yields a storage-stable emulsifiable concentrate which may be stored and later diluted with water to yield a ready-to-use composition.

The present formulation is a foliar applied, non-selective herbicide which may be sprayed upon unwanted weeds and grasses. Before use, an emulsifiable concentrate is diluted in water to achieve an active ingredient concentration in the range of approximately 1-8% fatty acid active ingredient. Most preferably, the concentration of active ingredient is in the range of 3-5%. The composition is most effective against young, succulent and actively growing weeds less than five inches in height. Several applications of the composition may be necessary to control certain grasses and established weeds. Maturing (flowering) and woody weeds are less susceptible to the formulation. Repeated applications of the composition may be necessary to kill perennial weeds. Examples of annual weeds controlable by this herbicidal composition include Lambsquarter, Pigweed, Mustard, Shepherd's purse, Spiney annual sowthistle, Pineapple weed, Scentless mayweed, Wild buckwheat, Green foxtail, Stinkweed, Corn spurry, Common groundsel, Red sheep sorrel, Common chickweed, Wild radish, Common purslane, Whitestem filaree, Little mallow, Volunteer oat, False flax and Barnyard grass.

Examples of perennial weeds controlable by this herbicidal composition include Spotted catsear, True dandelion, Narrow-leaf plantain, Curled dock, Horsetail, Mouse-eared chickweed, Lupine, Clovers, Perennial ryegrass, Thistles and Quackgrass.

The herbicidal formulation of this invention may be applied by conventional spraying means. The formulation is most effective when applied to thoroughly cover all of the plant foliage. Most succulent annual weeds and grasses 5" or less in height, and top kill of perennials, can be controlled with a spray volume of 8% v/v (3.2% active ingredient v/v). Larger annual weeds, weeds in dense stands, and more difficult to control perennials may require a spray volume in the range of 10-15% v/v spray solution.

The following non-limiting examples serve to further describe the invention.

EXAMPLE 1

An emulsifiable concentrate of herbicidal formulation A of Table I was prepared. The composition was diluted with water such that the concentration of the fatty acid active ingredient was reduced to 3%, 4%, 5% and 6% and the other components were commensurately reduced. The compositions were applied to the weeds shown in Table II using a trigger sprayer, sprayed to thorough wetting (i.e., about 74-193 ml/m$^3$ (80-200 gallons per acre)).

TABLE II

| Common Name | Size (inches) | Growth Stage (true leaf) | Infestation (avg. occur. %) |
|---|---|---|---|
| Corn Spurry | 2 | 2-4 | 40 |
| Wild mustard | 5 | 5-7 | 25 |
| Quackgrass | 20 | 3-4 | 20 |
| Redroot pigweed | 1 | 3-5 | <5 |
| Red clover | 4 | 8-12 | <5 |
| Narrow-leaf plantain | 4-6 | 3-30 | <5 |
| Spotted catsear | rosette | 4-15 | <5 |
| Red sorrel | — | 10-20 | <5 |
| False flax | 4 | 15-20 | <5 |

Each plot, 1.5 m×0.8 in size, to which the diluted emulsion of Formulation A was applied was arranged in a randomized complete block design. The percent weed control was recorded for active ingredient concentrations of 3, 4, 5 and 6 percent, measured at 3 and 10 days after treatment (D.A.T.) These data are shown Table III.

TABLE III

| | Percent Weed Control by Diluted Emulsions of Formulation A of Various Weed Species | | | | | | | |
|---|---|---|---|---|---|---|---|---|
| | 3 D.A.T. % Active Ingredient | | | | 10 D.A.T. % Active Ingredient | | | |
| Weed Species | 3 | 4 | 5 | 6 | 3 | 4 | 5 | 6 |
| % Mean Weed Control[1] | 90 | 94 | 94 | 96 | 85 | 88 | 85 | 85 |
| Corn spurry | 98 | 98 | 99 | 99 | 94 | 98 | 99 | 99 |
| Wild mustard | 95 | 97 | 98 | 99 | 88 | 98 | 99 | 97 |
| Quackgrass | 93 | 95 | 95 | 94 | 34 | 45 | 45 | 50 |
| Redroot pigweed | 100 | 100 | 100 | 100 | 87 | 100 | 100 | 100 |
| Red clover | * | * | 79 | 93 | * | * | 50 | 30 |
| Narrow-leaf plantain | * | * | 100 | * | * | * | 95 | * |
| Spotted catsear | 95 | 97 | 97 | 97 | 66 | 79 | 70 | 76 |
| Red Sorrel | 97 | 100 | 100 | 99 | 90 | 100 | 76 | 99 |
| False flax | 99 | 100 | 100 | 99 | 100 | 100 | 100 | 100 |

*All data presented as mean of 4 replications: 0% = no control, 100% = complete control.
*Insufficient plant numbers to provide accurate means.
[1]Mean weed control is reduced at 10 days after treatment due to regrowth of perennials: quackgrass, clover, plantain, catsear.

EXAMPLE II

Emulsifiable concentrates of herbicidal formulations A and C of Table I were prepared. The compositions were diluted with water and ready-to-use emulsions having approximately 3.6% active ingredient were prepared. The compositions were applied to thoroughly set the weed species of Table IV (i.e., about 80-190 gallons per acre) using a trigger sprayer.

TABLE IV

| Common Name | Size (inches) | Growth Stage (true leaf) | Infestation (% occurrence) |
| --- | --- | --- | --- |
| Corn spurry | 4–5 | 80–100 | 30 |
| Barnyard grass | 6–8 | 4–5 | 15 |
| Spotted catsear | rosette | 5–10 | 15 |
| Redroot pigweed | 1–2 | 5–7 | 8 |
| Mustard | 2–3 | 5–7 | <5 |
| Clover | 2–3 | 4–6 | <5 |
| Flax (false) | 4–6 | 10–20 | <5 |
| Shepherd's purse | 2–3 | 6–8 | <5 |
| Quackgrass | 4–6 | 4 | <5 |

The plots, 0.8 m ×0.8 m, to which the diluted emulsion of Formulations A and C were applied were arranged in a randomized complete block design. The percent weed control was recorded four days after spraying, and these data are displayed in Table V.

TABLE V

Percent Weed Control By Diluted Emulsions of Formulations A and C of Various Weed Species

| Weed Species | Form A-3.6% ai | Form C-3.6% ai |
| --- | --- | --- |
| % Mean weed control | 92 | 95 |
| Corn spurry | 97 | 97 |
| Barnyard grass | 97 | 97 |
| Spotted catsear | 98 | 97 |
| Redroot pigweed | 97 | 99 |
| Wild mustard | 92 | 99 |
| Clover | 90 | 97 |
| False flax | 98 | 94 |
| Shepherd's purse | 92 | 92 |
| Quackgrass | 97 | 92 |

All data presented as a mean of 4 replications: 0% = no control, 100% = plant death (complete control).

What is claimed is:

1. An environmentally compatible, non-selective herbicidal composition, suitable for emulsification in water prior to use, consisting essentially of:
   a herbicidally effective amount of a monocarboxylic fatty acid component of at least two fatty acids selected from the group consisting of caprylic, pelargonic, capric, undecanoic and lauric acids;
   an emulsifier component; and
   an oil component selected from the group consisting of triglyceridies, terpenoids and paraffinic mineral oils.

2. The composition of claim 1, further comprising water.

3. The composition of claim 1 comprising a concentrate having approximately 20–80% fatty acid, 15–75% oil component and 2–10% emulsifier component.

4. The composition of claim 3 comprising approximately 40% fatty acid component, 55% oil component and 5% emulsifier component.

5. The composition of claim 3 wherein the fatty acid component is predominantly pelargonic acid.

6. The composition of claim 5 wherein the oil is a triglyceride selected from the group consisting of cottonseed oil, coconut oil, soybean oil, corn oil, sunflower oil, olive oil, grapeseed oil, rapeseed oil, and mustard oil.

7. The composition of claim 5 wherein the oil is a terpenoid selected from the group consisting of pine oil, eucalyptus oil, orange oil and cedar oil.

8. The composition of claim 3 wherein the fatty acid component comprises approximately 94% pelargonic acid, 4% caprylic acid and 2% capric acid.

9. The composition of claim 3 wherein the emulsifier component is selected from the group consisting of anionic emulsifiers, non-ionic emulsifiers and mixtures thereof.

10. The composition of claim 8 wherein the concentrate is diluted with water to obtain a ready-to-use emulsion having approximately 1–8 weight percent fatty acid component, approximately 1.3 to 11.0 weight percent oil component and approximately 0.125 to 1.0 weight percent emulsifier.

11. An environmentally compatible herbicidally active emulsifiable concentrate consisting essentially of:
   approximately 40 weight percent of a herbicidally effective, fatty acid component having a predominant amount of pelargonic acid and a minor amount of one or more fatty acids having between 8 and 12 carbon atoms;
   approximately 55 weight percent of an oil component selected from the group consisting of cottonseed oil, pine oil and a paraffinic mineral oil; and
   approximately 5% emulsifier component; said concentrate being herbicidally non-selective.

12. An environmentally compatible ready-to-use, non-selective herbicidally active composition consisting essentially of:
   approximately 1–8 weight percent of a herbicidally effective fatty acid active ingredient component having a predominant amount of pelargonic acid and a minor amount of one having between 8 and 12 carbon atoms;
   approximately 1.3 to 11.0 weight percent of an oil component selected from the group consisting of cottonseed oil, pine oil and paraffinic mineral oil;
   approximately 0.125 to 1.0 weight percent of an emulsifier component; and
   water to 100 percent.

* * * * *

UNITED STATES PATENT AND TRADEMARK OFFICE
CERTIFICATE OF CORRECTION

PATENT NO.  : 5,035,741
DATED       : July 30, 1991
INVENTOR(S) : Puritch et al.

It is certified that error appears in the above-identified patent and that said Letters Patent is hereby corrected as shown below:

Column 6, line 66, please delete "set" and insert --wet--.

Column 6, line 67, please delete "80" and insert --85--.

Signed and Sealed this

Sixteenth Day of February, 1993

Attest:

STEPHEN G. KUNIN

*Attesting Officer*        Acting Commissioner of Patents and Trademarks